(12) United States Patent
Majercak (10) Patent No.: US 7,942,920 B2
(45) Date of Patent: *May 17, 2011

(54) STENT WITH NESTED FINGERS FOR ENHANCED VESSEL COVERAGE

(75) Inventor: David C. Majercak, Stewartsville, NJ (US)

(73) Assignee: Cordis Corporation, Bridgewater, NJ (US)

( * ) Notice: Subject to any disclaimer, the term of this patent is extended or adjusted under 35 U.S.C. 154(b) by 1297 days.

This patent is subject to a terminal disclaimer.

(21) Appl. No.: 10/373,489

(22) Filed: Feb. 25, 2003

(65) Prior Publication Data

US 2004/0167609 A1 Aug. 26, 2004

(51) Int. Cl.
*A61F 2/01* (2006.01)
(52) U.S. Cl. ...................... 623/1.15; 606/194
(58) Field of Classification Search .................. 606/191, 606/192, 194, 195, 198, 108; 623/1.15, 1.12, 623/1.16, 1.17, 1.2, 1.42, 1.43
See application file for complete search history.

(56) References Cited

U.S. PATENT DOCUMENTS

| | | | |
|---|---|---|---|
| 5,192,307 A | 3/1993 | Wall | |
| 5,354,308 A | 10/1994 | Simon et al. | |
| 5,397,355 A | 3/1995 | Marin et al. | |
| 5,733,330 A | 3/1998 | Cox | |
| 5,766,239 A | 6/1998 | Cox | |
| 5,800,526 A | 9/1998 | Anderson et al. | |
| 5,911,732 A | 6/1999 | Hojeibane | |
| 5,938,682 A * | 8/1999 | Hojeibane et al. | 606/198 |
| 5,997,563 A | 12/1999 | Kretzers | |
| 6,022,371 A | 2/2000 | Killion | |
| 6,033,435 A | 3/2000 | Penn et al. | |
| 6,033,436 A | 3/2000 | Steinke et al. | |
| 6,066,167 A | 5/2000 | Lau et al. | |
| 6,083,258 A | 7/2000 | Yadav | |
| 6,129,754 A | 10/2000 | Kanesaka et al. | |
| 6,129,755 A * | 10/2000 | Mathis et al. | 623/1.15 |
| 6,156,062 A | 12/2000 | McGuinness | |
| 6,171,334 B1 | 1/2001 | Cox | |
| 6,174,316 B1 | 1/2001 | Tuckey et al. | |
| 6,190,403 B1 * | 2/2001 | Fischell et al. | 623/1.16 |
| 6,210,429 B1 | 4/2001 | Vardi et al. | |
| 6,251,134 B1 | 6/2001 | Alt et al. | |
| 6,258,116 B1 | 7/2001 | Hojeibane | |
| 6,277,078 B1 * | 8/2001 | Porat et al. | 600/486 |
| 6,325,826 B1 | 12/2001 | Vardi et al. | |

(Continued)

FOREIGN PATENT DOCUMENTS

DE 29701758 U1 2/1997

(Continued)

OTHER PUBLICATIONS

European Search Report EP05253501 dated Oct. 25, 2005.

(Continued)

*Primary Examiner* — Michael J Milano
*Assistant Examiner* — Victor X Nguyen
(74) *Attorney, Agent, or Firm* — Louis J. Capezzuto (57) ABSTRACT

A stent having a lattice and defining a substantially cylindrical configuration has a first open end and a second open end. The lattice has a collapsed configuration and an expanded configuration and a plurality of adjacent hoops. Each hoop has a plurality of adjacent loops and a plurality of bridges connect adjacent hoops. A plurality of extensions are provided on the lattice. And, each of the hoops, bridges and extensions define a cell.

25 Claims, 6 Drawing Sheets

U.S. PATENT DOCUMENTS

| | | |
|---|---|---|
| 6,346,089 B1 | 2/2002 | Dibie |
| 6,599,314 B2 * | 7/2003 | Mathis .................. 623/1.11 |
| 6,599,316 B2 | 7/2003 | Vardi et al. |
| 6,673,107 B1 | 1/2004 | Brandt et al. |
| 6,676,696 B1 | 1/2004 | Marotta et al. |
| 6,942,681 B2 * | 9/2005 | Johnson .................. 606/194 |
| 2001/0003161 A1 | 6/2001 | Vardi et al. |
| 2001/0004706 A1 | 6/2001 | Hojeibane |
| 2001/0016767 A1 | 8/2001 | Wilson et al. |
| 2002/0042650 A1 | 4/2002 | Vardi et al. |
| 2002/0062147 A1 * | 5/2002 | Yang .................. 623/1.13 |
| 2002/0111671 A1 | 8/2002 | Stenzel |
| 2002/0133183 A1 | 9/2002 | Lentz et al. |
| 2003/0009213 A1 * | 1/2003 | Yang .................. 623/1.13 |

FOREIGN PATENT DOCUMENTS

| | | |
|---|---|---|
| DE | 19653721 A1 | 4/1998 |
| DE | 19728337 A | 1/1999 |
| DE | 199 50 756 A1 | 2/1999 |
| DE | 19728337 A1 | 7/1999 |
| EP | 1179323 A2 | 2/2002 |
| EP | 1267748 B1 | 1/2003 |
| EP | 1503700 | 11/2003 |
| WO | 98/26732 A1 | 6/1998 |
| WO | WO 98/26732 A1 | 6/1998 |
| WO | WO 00/59405 A1 | 10/2000 |
| WO | WO 01/30271 A2 | 5/2001 |
| WO | 03/055414 A1 | 7/2003 |
| WO | WO 03/055414 A1 | 7/2003 |
| WO | 03/063924 A1 | 8/2003 |
| WO | WO 03/063924 A1 | 8/2003 |
| WO | 03/094798 A1 | 11/2003 |
| WO | WO 03/094798 A1 | 11/2003 |
| WO | 2004/032801 A1 | 4/2004 |
| WO | WO 2004/032801 A1 | 4/2004 |

OTHER PUBLICATIONS

European Search Report EP 04 250 845.7 dated Apr. 16, 2007.
European Search Report EP 04 25 0845 dated Jun. 20, 2006.
European Search Report re: EP02253789 dated Jan. 16, 2003.

* cited by examiner

STENT WITH NESTED FINGERS FOR ENHANCED VESSEL COVERAGE

FIELD OF THE INVENTION

The present invention relates, in general, to intraluminal medical devices, and, more particularly, to a new and useful stent having one or more extensions or fingers for enhancing vessel coverage and preventing plaque or tissue prolapse.

BACKGROUND ART

A stent is commonly used as a tubular structure left inside the lumen of a duct to relieve an obstruction. Commonly, stents are inserted into the lumen in a non-expanded form and are then expanded autonomously (or with the aid of a second device) in situ. When used in coronary artery procedures for relieving stenosis, stents are placed percutaneously through the femoral artery. In this type of procedure, stents are delivered on a catheter and are either self-expanding or, in the majority of cases, expanded by a balloon. Self-expanding stents do not need a balloon to be deployed. Rather the stents are constructed using metals with spring-like or superelastic properties (i.e., Nitinol), which inherently exhibit constant radial support. Self-expanding stents are also often used in vessels close to the skin (i.e., carotid arteries) or vessels that can experience a lot of movement (i.e., popliteal artery). Due to a natural elastic recoil, self-expanding stents withstand pressure or shifting and maintain their shape.

As mentioned above, the typical method of expansion for balloon expanded stents occurs through the use of a catheter mounted angioplasty balloon, which is inflated within the stenosed vessel or body passageway, in order to shear and disrupt the obstructions associated with the wall components of the vessel and to obtain an enlarged lumen.

Balloon-expandable stents involve crimping the device onto an angioplasty balloon. The stent takes shape as the balloon is inflated and remains in place when the balloon and delivery system are deflated and removed.

In addition, balloon-expandable stents are available either pre-mounted or unmounted. A pre-mounted system has the stent already crimped on a balloon, while an unmounted system gives the physician the option as to what combination of devices (catheters and stents) to use. Accordingly, for these types of procedures, the stent is first introduced into the blood vessel on a balloon catheter. Then, the balloon is inflated causing the stent to expand and press against the vessel wall. After expanding the stent, the balloon is deflated and withdrawn from the vessel together with the catheter. Once the balloon is withdrawn, the stent stays in place permanently, holding the vessel open and improving the flow of blood.

In the absence of a stent, restenosis may occur as a result of elastic recoil of the stenotic lesion. This problem is not eliminated with a stent since the prolapse of plaque or tissue within the stent itself will occur in the unsupported areas called "cells". All stents have cells and they generally fall into two groups: open-cell or closed-cell designs or architectures which facilitate plaque or tissue prolapse to varying degrees. Closed-cell refers to the fact that each opening or cell is isolated from any other by a full-connected metal perimeter. An open-cell design has openings or cells that can communicate with other cells around the circumference since they are not fully surrounded by a metal perimeter (there are gaps or "open" passages that lead to other cells). Although a number of stent designs have been reported, these designs have suffered from prolapse and a number of other limitations.

Additionally, the flexibility of the stent is important for maneuvering the stent through a vessel and less flexible stents are a drawback. The general construction or design of the stent, i.e. the open-cell or closed-cell design, is indicative of the ultimate flexibility or stiffness of the stent (open cell stents are more flexible). Another consideration is the cell size/shape as it pertains to accessing vessel side branches ("side branch access"). As is known in the field, side branch access is obtained by placing a balloon within one of the cells and expanding the structure or framework defining the cell with the balloon by inflating the balloon at a high pressure wherein the expanded cell is dilated to a larger size than the original expanded size of the cell. If the dilated cell size is too small, the less the ability to provide side branch access when the stent is expanded or deployed. If the cell deforms too much when ballooned, uniform coverage around the side branch will not be maintained and cause additional prolapse.

Accordingly, to date, there have not been any stent designs, that specifically address these drawbacks in an efficient and cost-effective manner. The invention described here is aimed at allowing small cell size with great flexibility without increasing prolapse.

BRIEF SUMMARY OF THE INVENTION

The present invention relates to an apparatus for stenting a vessel which is a new and useful stent having a lattice of interconnecting elements defining a substantially cylindrical configuration. The lattice has a first open end and a second open end wherein the lattice is moveable between a crimped state and an expanded or deployed state.

The stent further comprises a plurality of bridges connecting the interconnecting elements wherein each bridge has at least one extension or finger thereon. In some embodiments, each extension or finger of each bridge is in juxtaposition with or is adjacent to, in a nested fashion with, an extension or finger of an adjacent bridge when the stent is in the crimped state. In these embodiments, each extension or finger of adjacent bridges are separated from each other and from an adjacent bridge when the stent is deployed or expanded to its expanded state.

The stent according to the present invention has interconnecting elements comprising a plurality of adjacent sections wherein each section comprises hoops. Each hoop comprises a plurality of loops and each hoop comprises at least one strut. In accordance with the present invention, the extensions or fingers are located on one or more of the interconnecting elements of the lattice. For example, the extensions may be located on a bridge, or anywhere on a hoop, for instance, on one or more of the loops, one or more of the struts, or any combination of these interconnecting elements. In accordance with the present invention, the extensions are designed to occupy locations within the cells of the stent in a manner that decreases or limits the maximum circular diameter within the cell upon expansion or deployment of the stent.

In accordance with the present invention, the closed-cell design embodiment and the open-cell design embodiments comprise a plurality of cells having a maximum cell diameter ranging from about 0.76 mm to about 1.22 mm when the stent is in the deployed or expanded state after the stent is expanded to an overall diameter of approximately 3.0 mm as measured along its longitudinal axis. Preferably, (when a side branch access procedure may be desired), the cell has a maximum cell diameter having a size which ranges from about 0.91 mm to about 1.12 mm when the stent is deployed such that the stent has an overall diameter of approximately 3.0 mm as measured along its longitudinal axis. Preferably, (with no side branches present), the stent is expanded such that the plurality of cells have a maximum cell diameter ranging from about 0.76 mm to about 1.02 mm when the stent is expanded to an overall diameter of approximately 3.0 mm (as measured along the longitudinal axis of the stent).

Additionally, when providing side branch access, the stent in accordance with the present invention, for those stents having a closed-cell design, the cell has a maximum cell diameter greater than 1.5 mm when the cell of the stent is dilated from the cell dilation procedure. Preferably, the stent has a cell having a maximum cell diameter ranging from about 1.5 mm to about 3.0 mm after after dilation of the cell as part of a cell dilation procedure. More preferably, the stent has a cell having a maximum cell diameter size of about or approximately 3.0 mm after dilation of the cell as part of a cell dilation procedure. Most preferably, after the deployment of the stent, the cell is dilated such that it has a maximum cell diameter ranging from about 3.0 mm to about 3.5 mm.

In accordance with the present invention, for those stents having an open-cell design, the cell has a maximum cell diameter size that is greater than 3.0 mm when the cell is dilated, for instance, as part of a side branch access procedure. Preferably, embodiments of open-cell design stents in accordance with the present invention comprise a cell having a maximum cell diameter ranging from about 3.0 mm to about 3.5 mm after dilating the cell.

In accordance with the present invention, the bridges have various configurations. In one preferred embodiment in accordance with the present invention, the bridges have a sinusoidal or sinusoid-shape configuration. Thus, each bridge has one or more apex thereon. In another preferred embodiment, there are two apex thereon. A pocket is on the underside of each apex which is sized in a sufficient manner and shaped to receive an extension or finger of an adjacent bridge when the stent is in its crimped state In these embodiments, each extension or finger is designed in a manner to fit within the pocket of an adjacent bridge and nest with another extension or finger of the adjacent bridge when the stent is in its crimped state. Accordingly, the extensions or fingers may take various alternative forms such as: linear, radial, arc-like, hoop-like, undulating patterns, dove-tail patterns or the like.

BRIEF DESCRIPTION OF THE DRAWINGS

The novel features of the invention are set forth with particularity in the appended claims. The invention itself, however, both as to organization and methods of operation, together with further objects and advantages thereof, may be best understood by reference to the following description, taken in conjunction with the accompanying drawings in which:

DETAILED DESCRIPTION OF THE INVENTION

As known in the art and best illustrated in FIGS. 1A-1D and 2A-2C, a stent 100,100a respectively is an expandable prosthesis for a body passageway. It should be understood that the terms "stent" and "prosthesis" are interchangeably used to some extent in describing the present invention, insofar as the method, apparatus, and structures of the present invention may be utilized not only in connection with an expandable intraluminal vascular graft for expanding partially occluded segments of a blood vessel, duct or body passageways, such as within an organ, but may so be utilized for many other purposes as an expandable prosthesis for many other types of body passageways. For example, expandable prostheses may also be used for such purposes as: (1) supportive graft placement within blocked arteries opened by transluminal recanalization, but which are likely to collapse in the absence of internal support; (2) similar use following catheter passage through mediastinal and other veins occluded by inoperable cancers; (3) reinforcement of catheter created intrahepatic communications between portal and hepatic veins in patients suffering from portal hypertension; (4) supportive graft placement of narrowing of the esophagus, the intestine, the ureters, the uretha, etc.; (5) intraluminally bypassing a defect such as an aneurysm or blockage within a vessel or organ; and (6) supportive graft reinforcement of reopened and previously obstructed bile ducts. Accordingly, use of the term "prothesis" encompasses the foregoing usages within various types of body passageways, and the use of the term "intraluminal graft" encompasses use for expanding the lumen of a body passageway. Further in this regard, the term "body passageway" encompasses any lumen or duct within the human body, such as those previously described, as well as any vein, artery, or blood vessel within the human vascular system.

The stent 100 (FIGS. 1A-1D) and 100a (FIGS. 2A-2D) comprises an expandable lattice structure made of any suitable material which is compatible with the human body and the bodily fluids (not shown) with which the stent 100 and 100a may come into contact. The lattice structure is an arrangement of interconnecting elements made of a material which has the requisite strength and elasticity characteristics to permit the tubular shaped stent 100 and 100a to be expanded from the crimped state shown in FIGS. 1A and 1C and FIG. 2B respectively to the deployed or expanded state as shown in FIG. 1D and FIG. 2C respectively and further to permit the stent 100 and 100a to retain its expanded state at an enlarged diameter. Suitable materials for the fabrication of the stent 100 and 100a include silver, tantalum, stainless steel, gold, titanium or any suitable plastic material having the requisite characteristics previously described.

The stent 100 and 100a may also comprise a superelastic alloy such as nickel titanium (NiTi, e.g., Nitinol). For stents 100 and 100a made of superelastic material, the superelastic design of the stent 100 and 100a make it crush recoverable and thus suitable as a stent or frame for any number of vascular devices for different applications.

Figure 1A:
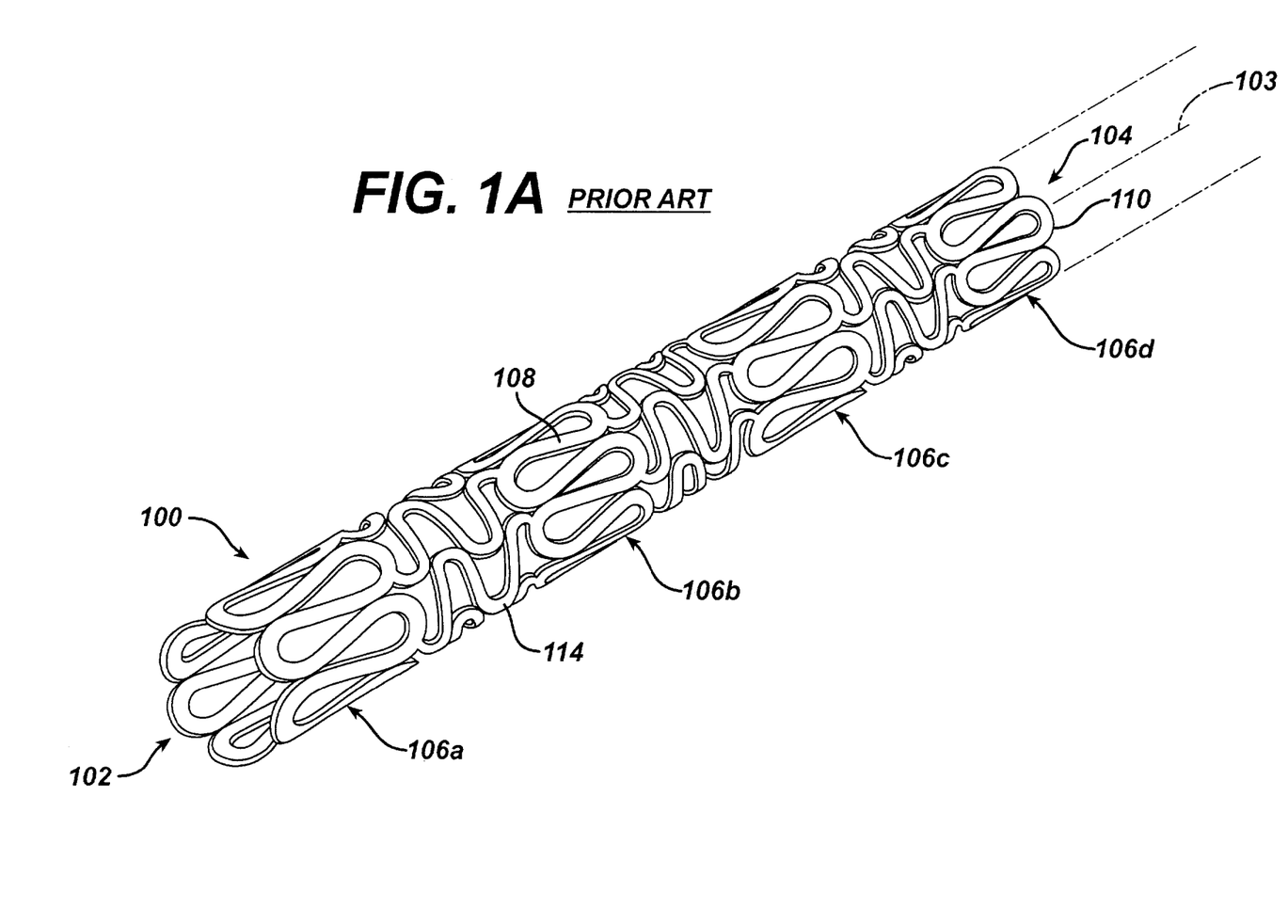
FIG. 1A is a perspective view of a prior art stent of a closed cell design in a crimped state.
Figure 1B:
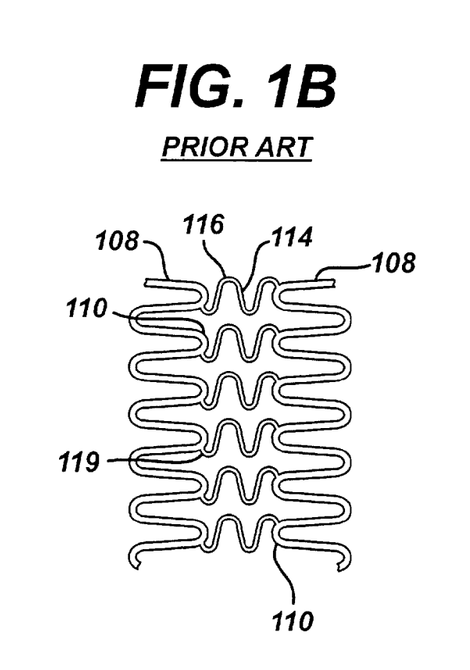
FIG. 1B is a partial side view of a section of the prior art stent of FIG. 1A in a configuration conducive for a polishing manufacturing step.
Figure 1C:
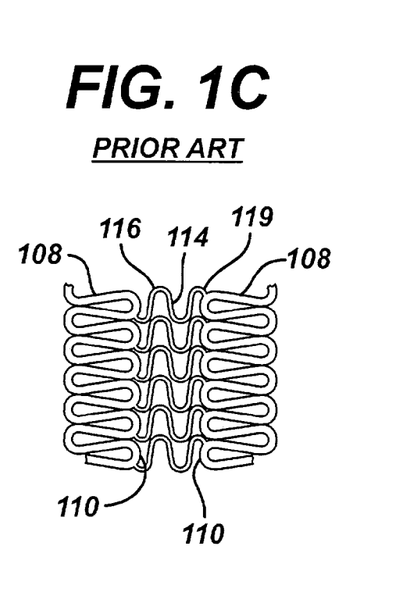
FIG. 1C is a partial side view of a section of the prior art stent of FIG. 1A in the crimped state.
Figure 1D:
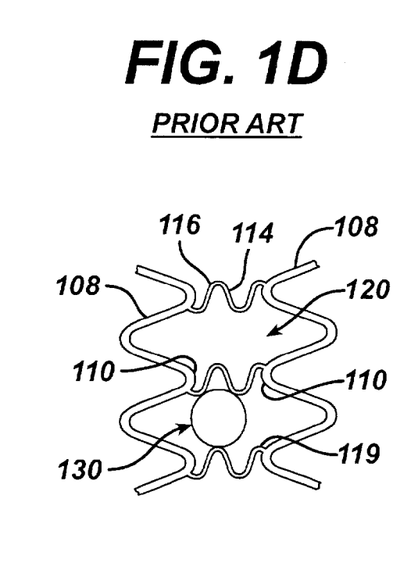
FIG. 1D is a partial side view of a section of the prior art stent of FIG. 1A in an expanded state defining a closed-cell having a maximum circular cell diameter.

The stent 100 and 100a comprises a tubular configuration formed by a lattice of interconnecting elements defining a substantially cylindrical configuration and having front and back open ends 102, 104 and defining a longitudinal axis 103 extending therebetween (FIG. 1A). The stent 100 (FIGS. 1A-1D) is known and has a closed-cell 120 (closed cell design) and the stent 100a (FIGS. 2A-2C) is known and has an open-cell 120a (open cell design). Characteristics of open and closed cell designs will be addressed in greater detail later in this disclosure. In its closed crimped state, the stent 100 and 100a has a first, smaller outer diameter for insertion into a patient and navigation through the vessels and, in its expanded (deployed) state, a second, larger outer diameter for deployment into the target area of a vessel with the second diameter being greater in size than the first diameter. The stent 100 and 100a comprises a plurality of adjacent hoops 106(a)-(d) extending between the front and back ends 102, 104. The hoops 106(a)-(d) include a plurality of longitudinally arranged struts 108 and a plurality of loops 110 connecting adjacent struts 108. Adjacent struts 108 are connected at opposite ends so as to form any desired pattern such as a substantially S or Z shape pattern. The plurality of loops 110 have a substantially semi-circular configuration and are substantially symmetric about their centers.

The stent 100 and 100a further comprises a plurality of flexible links or bridges 114 and 114a respectively. The bridges 114 and 114a connect adjacent hoops 106(a)-(d). The details of the bridges 114 and 114a are more fully described below. The term "flexible link" or "bridges" have the same meaning and can be used interchangeably. There are many types or forms for the flexible links or bridges 114. For example, the bridges 114 and 114a may be an S-Link (having an S-Shape or being sinusoidal shape), a J-Link (having a J-Shape), and N-Link (having an N-shape), M-Link (M-Shaped) or W-Link (W-Shaped), wherein each of these configurations can also be inverted.

Figure 2A:
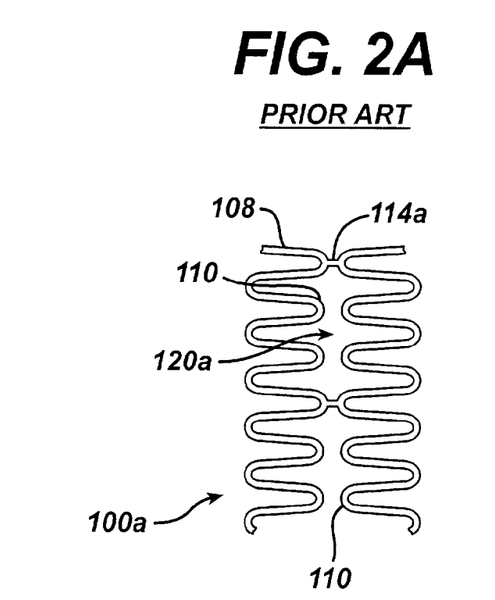
FIG. 2A is a partial side view of a prior art stent of an open-cell design in a configuration conducive for a polishing manufacturing step.
Figure 2B:
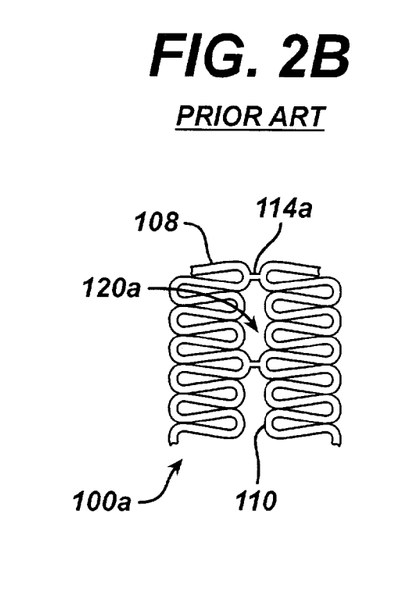
FIG. 2B is a partial side view of the prior art stent of FIG. 2A in a crimped state.
Figure 2C:
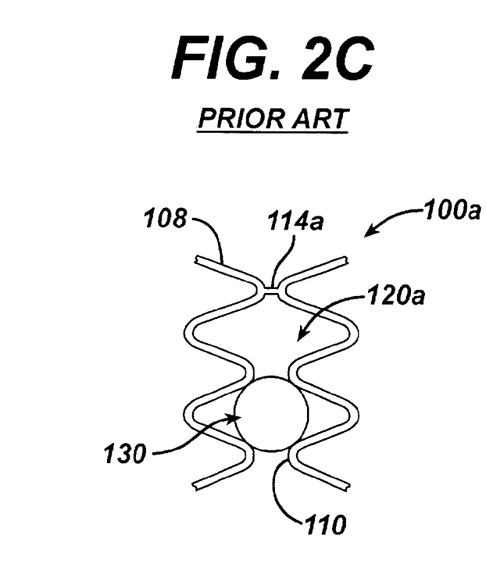
FIG. 2C is a partial side view of the prior art stent of FIG. 2A in an expanded state defining an open cell having a maximum circular cell diameter.

In general, bridges 114 and 114(a) respectively are used to connect adjacent hoops 106(a)-106(d). Each bridge comprises two ends wherein one end of the bridge is attached to a first hoop for example 106(a), and the other end of the bridge is attached to a second, adjacent hoop, for example 106(b), as shown in FIG. 1A. The attachment points for the bridge can be at any location on the hoops 106(a)-106(d), for instance, connection points at or directly on loops 110 or struts 108. Thus, bridges that connect at every loop 110 of adjacent hoops 106(a)-106(d), define a closed-cell as shown in FIGS. 1A-1D. Moreover, bridges that connect adjacent hoops 106(a)-106(d) at only a select number of loops 110, e.g. a set number of loops 110 without interconnecting bridges, define an open-cell such as illustrated in FIGS. 2A-2C.

The above-described geometry distributes strain throughout the stent 100 and 100a, prevents metal to metal contact where the stent 100 and 100a is bent, and minimizes the opening between the features of the stent 100 and 100a; namely, struts 108, loops 110 and bridges 114 114a respectively. The number of and nature of the design of the struts, loops and bridges are important design factors when determining the working properties and fatigue life properties of the stent 100 and 100a. It was previously thought that in order to improve the rigidity of the stent, struts should be large, and thus there should be fewer struts 108 per hoop 106(a)-106(d). However, it is now known that stents 100 having smaller struts 108 and more struts 108 per hoop 106(a)-106(d) improve the construction of the stent 100 and provide greater rigidity. Preferably, each hoop 106(a)-106(d) has between twenty-four (24) to thirty-six (36) or more struts 108. It has been determined that a stent having a ratio of number of struts per hoop to strut length which is greater than four hundred has increased rigidity over other known stents which typically have a ratio of under two hundred. The length of a strut is measured in its compressed or crimped state parallel to the longitudinal axis 103 of the stent 100 as illustrated in FIG. 1A.

FIG. 1D and FIG. 2C illustrate the stent 100 and 100a in its deployed or expanded state. As may be seen from a comparison between the stent configurations illustrated in FIG. 1C and FIG. 2B respectively and the stent configuration illustrated in FIG. 1D and FIG. 2C respectively, the geometry of the stent 100 and 100a changes quite significantly as it is deployed from its crimped state to its expanded or deployed state. As the stent undergoes diametric change, the strut angle and strain levels in the loops 110 and bridges 114 and 114a are affected. Preferably, all of the stent features will strain in a predictable manner so that the stent 100 is reliable and uniform in strength. In addition, it is preferable to minimize the maximum strain experienced by the struts 108, loops 110 and bridges 114 and 114a since Nitinol properties are more generally limited by strain rather than by stress.

With respect to stent designs in general, there are regular connections which refer to bridges 114 and 114a that include connections to every inflection point around the circumference of a structural member, i.e. the loops 110 of adjacent hoops 106(a)-106(d).

Additionally, for stents having an open-cell design, e.g. 100a, there are periodic connections for the stent bridges 114a that include connections to a subset of the inflection points (loops 110) around the circumference of the structural members (lattice). With respect to these period connections, the connected inflection points (loops 110) alternate with unconnected inflection points (loops 110) in some defined pattern.

Moreover, in general, bridges can join the adjacent structural members at different points. For example, in a "peak-peak" connection, the bridges 114 and 114a join the adjacent structural members or loops 110 by joining the outer radii formed by adjacent loops 110. Alternatively, the bridges 114 and 114a can form "peak-valley" connections wherein the bridges 114 and 114a join the outer radii of one inflection point (of a structural member) to the inner radii of the inflection point of an adjacent structural member.

Furthermore, the bridges 114 and 114a between adjacent structural members, i.e. hoops 106, define cell patterns as briefly mentioned above. For example, bridges 114 may define a "closed-cell" formed where all of the internal inflection points, e.g. loops 110 are connected by bridges 114 as shown in FIGS. 1A-1D.

Furthermore, it is common for bridges 114 to form a "closed-cell" which is in essence a sequential ring construction wherein all internal inflection points of the structural members are connected by bridges 114. Such a condition is only possible with regular peak-to-peak connections. The closed-cells permit for plastic deformation of the stent 100 during bending thereby allowing adjacent structural members to separate or nest together in order to more easily accommodate changes in shape of the stent 100. The primary advantages of a closed-cell stent design is that it provides optimal scaffolding and a uniform surface regardless of the degree of bending of the stent. Depending on the specific features of a closed-cell design, the stent 100 may be less flexible than a stent with an open-cell design.

For those known stents 100 having a closed-cell design, as best represented by example in FIGS. 1A-1D, the stent 100 has a plurality of cells 120 whose size can be defined by a maximum circular diameter 130. The maximum circular diameter 130 is determined by the largest circle that can fit within the area defined by the cell 120. For a closed-cell design stent 100, the cell 120 has a maximum circular diameter 130 that tends to have a size which is approximately greater than 1.22 mm when the stent 100 is deployed to an expanded or deployed state, i.e. expanded to an overall stent diameter of approximately 3.0 mm (as measured along longitudinal axis 103) and some measurements have shown the cell 120 to have maximum circular cell diameter 130 as high as 1.32 mm when the stent 100 is deployed to the expanded state, i.e. stent 100 expanded to an overall stent diameter of approximately 3.0 mm along its longitudinal axis 103, as shown in FIG. 1D.

As shown in FIGS. 2A-2C, the cell design of an open-cell stent 100a (shown having peak-to-peak connections) has innumerable hybrid combinations of connection points. As is known, in open-cell designs, such as with the stent 100a, the unconnected structural elements contribute to longitudinal flexibility of the stent 100a. Additionally, the open-cell stent 100a of FIGS. 2A-2C has a cell 120a with a maximum circular cell diameter 130a having a size that is approximately greater than 1.32 mm when the stent 100a is deployed to its expanded state at an overall stent diameter of about or approximately 3.0 mm, i.e. 3.0 mm diameter along the stent longitudinal axis 103 after deployment.

One interesting aspect relating to the closed-cell design for stents is that the smaller the cell size (such as the maximum circular cell diameter), the less flexible is the stent. Thus, smaller cell size for closed-cell stents results in low bend ratios and increased stiffness overall for the stent. Thus, stents having relatively small cell sizes (in a closed-cell design) tend to be more difficult to maneuver through vessels especially tortuous vessels. One example of one of these type of stents having a very small cell size and extremely low flexibility (increased stiffness) is the NIR™ stent (sold by Boston Scientific Corporation). For example, this stent has a cell having an estimated maximum circular cell diameter of approximately 0.99 mm when the stent is deployed (deployed/expanded to an overall stent diameter of approximately 3.0 mm) and is known to be very stiff and have low flexibility.

Turning now to the present invention, the same reference numerals will be used to designate like or similar features for a stent 100b (FIGS. 3A-3D), 100c (FIGS. 4A-4C) and 100d (FIG. 4D) in accordance with the present invention as best illustrated in these figures. One novel stent 100b in accordance with the present invention is a closed-cell design stent as best illustrated in FIGS. 3A-3D. By way of example, the stent 100b utilizes bridges 114b that connect every loop 110 of adjacent hoops. By way of example, the bridge 114b is shown as a sinusoidal-shaped bridge, however, the bridge 114b can comprise any particular shape or configuration such as the shapes addressed above.

Figure 3A:
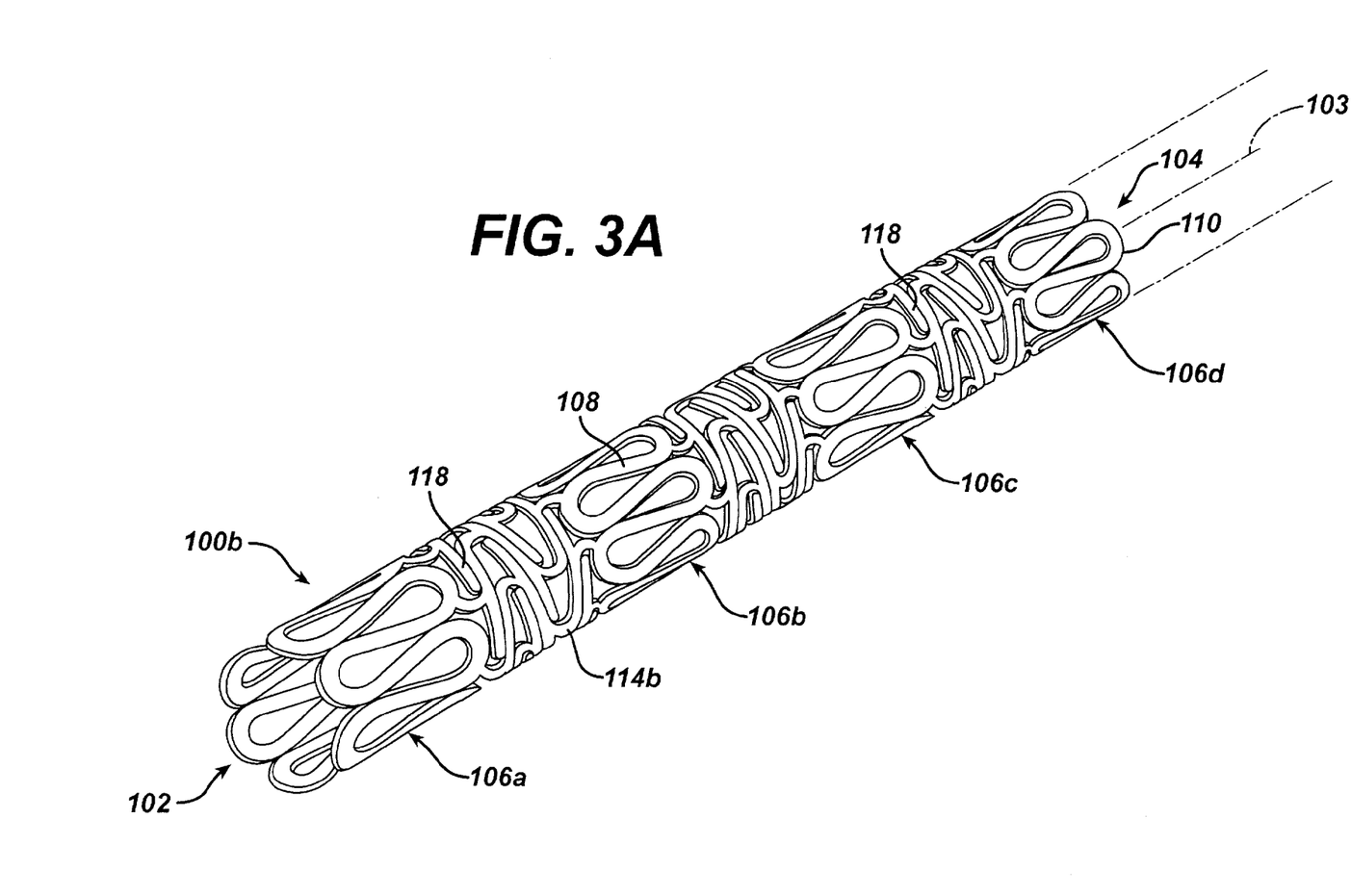
FIG. 3A is a perspective view of a stent having a closed-cell design and one or more extensions in accordance with the present invention.
Figure 3B:
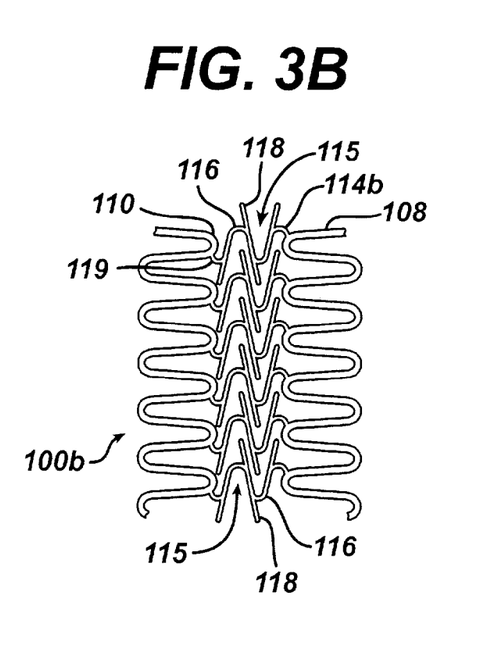
FIG. 3B is a partial side view of the stent of FIG. 3A in a configuration conducive for a polishing manufacturing step in accordance with the present invention.
Figure 3C:
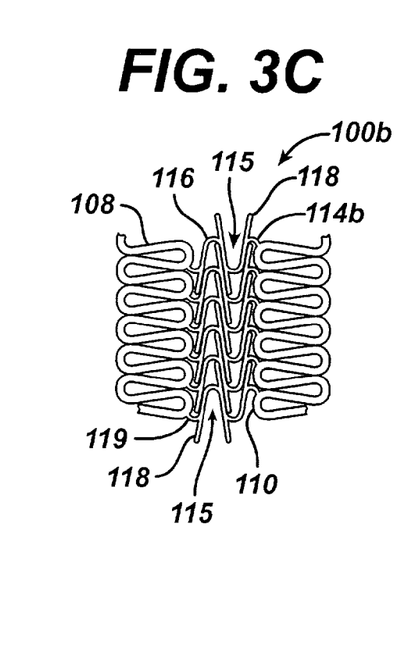
FIG. 3C is a partial side view of the stent of FIG. 3A in a crimped state in accordance with the present invention.
Figure 3D:
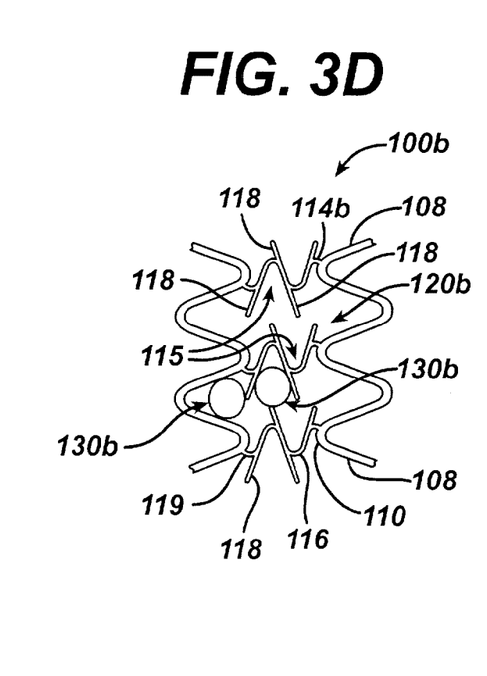
FIG. 3D is a partial side view of the stent of FIG. 3A in an expanded state and having a cell with a maximum circular cell diameter in accordance with the present invention.

Each bridge 114b has a finger or extension 118 integrally formed therewith and contiguous with the bridge 114b. In accordance with the present invention, the extension 118 is a finger or finger-like projection from the bridge 114b. Each bridge 114b can include more than one extension 118 extending therefrom. For instance, the sinusoidal-shape bridge 114b includes one or more apex 116 and a pocket 115, which is a space directly beneath or underlying the apex 116 as shown in FIGS. 3B-3D. Although the extensions 118 are shown as being linear in configuration, the extensions 118 can take any desired form, shape or configuration. In this example, the extensions 118 are linear and extend into the pocket 115 of an adjacent bridge 114b such that the extensions 118 nest with each other as best shown in FIG. 3C. Although the extensions or fingers 118 are depicted in a substantially linear configuration or shape, the extension 118 may take the form of any desired shape, for instance: linear, radial, arc-like, hoop-like, undulating patterns, dove-tail patterns or the like, etc. For efficiency purposes, such as ensuring compactness and low profile for crimping the stent 100b onto its delivery device or catheter, it is important that the extensions 118 of adjacent bridges 114b lie in juxtaposition with an adjacent extension 118 of an adjacent bridge 114b. Thus, adjacent bridges 114b will have adjacent extensions 118 that nest with each other when the stent 100b is in the crimped state as shown in FIG. 3C. The side-by-side alignment of adjacent extensions 118 of adjacent bridges 114b is facilitated by the shape of the bridges 114a (in this example a linear shape embodiment) whereby at the underside of each apex 116 resides a bridge pocket 115 of sufficient size and configuration in order to receive and accommodate an adjacent extension (finger) 118 of an adjacent bridge 114a as shown in FIGS. 3B and 3C. At a minimum, the extensions 118 will fit within the pocket 115 of adjacent bridges 114a in the crimped state.

As shown in FIG. 3D, the stent 100b in accordance with the present invention is a closed-cell design stent defining a plurality of cells 120b wherein each cell 120b has a maximum circular cell diameter 130b directly affected by the extensions 118 extending into and positioned within the cell 120b. Accordingly, when the stent 100b is deployed to its expanded state such that the overall diameter for the stent 100b is approximately 3.0 mm (stent diameter of approximately 3.0 mm along the longitudinal axis 103), the cell 120b has a maximum circular cell diameter 130b having a size which ranges from about 0.76 mm to about 1.22 mm as best shown in FIG. 3D. And, preferably, especially if a side branch access procedure may be desired, the cell 120b has a maximum circular cell diameter 130b having a size which ranges from about 0.91 mm to about 1.12 mm when the stent 100b is deployed to its expanded state, i.e. such that the stent 100b has an overall diameter of approximately 3.0 mm after its deployment (3.0 mm overall diameter for the stent 100b along its longitudinal axis 103). Preferably, when no side branches are present, the cell 120b has a maximum circular diameter ranging from approximately 0.76 mm to approximately 1.02 mm upon expansion of the stent 100b to about 3.0 mm diameter especially when no side branch access procedures is desired or needed.

After the stent 100b is expanded, it may be desirable to conduct a cell dilation procedure, for example, a side branch access procedure. Accordingly, the cell 120b itself is required to be dilated. Thus, when the cell 120b of the stent 100b is dilated through a cell dilation procedure, for example, a side branch access procedure, the cell 120b is dilated to a maximum circular cell diameter 130b having a size approximately greater than 1.5 mm. And, preferably, cell 120b is dilated to a maximum circular cell diameter 130b having a size which ranges from about 1.5 mm to about 3.0 mm when the cell 120b is dilated (e.g. as part of a side branch access procedure). And, more preferably, the cell 120b has a maximum circular that is approximately 3.0 mm. And, most preferably, the cell 120b is dilated to a maximum circular cell diameter 130b having a size which is dilated to a size ranging from about or approximately 3.0 mm to approximately 3.5 mm.

Additionally, the extensions 118 can also be located on either the loops 110, and struts 108 as well as the bridges 114b or in any combination thereof.

In accordance with the present invention, the stent 100b (FIGS. 3A-3D), stent 100c (FIGS. 4A-4C) and stent 100d (FIG. 4D), have extensions 118, 118a, 118b and 118c respectively located on one or more of the following components of the stent lattice: the bridges 114b and 114c respectively, the hoops 106(a)-106(d), the loops 110, and/or the struts 108. Moreover, the components of the stent lattice and the extensions 118, 118a, 118b and 118c respectively have drug coatings or drug and polymer coating combinations that are used to deliver the drug, i.e. therapeutic and/or pharmaceutical agents including: antiproliferative/antimitotic agents including natural products such as vinca alkaloids (i.e. vinblastine, vincristine, and vinorelbine), paclitaxel, epipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP)II$_b$III$_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF) platelet derived growth factor (PDGF), erythropoetin,; angiotensin receptor blocker; nitric oxide donors; anti-sense oligionucleotides and combinations thereof; cell cycle inhibitors, mTOR inhibitors, and growth factor signal transduction kinase inhibitors. It is important to note that one or more of the lattice components (e.g. hoops, loops, struts, bridges and extensions) are coated with one or more of the drug coatings or drug and polymer coating combinations.

Additionally, the extensions 118, 118a, 118b and 118c respectively provide uniformity for the stent 100b, 100c and 100d in accordance with the present invention, however, do not change the stress for strain on the stent 100b, 100c and 100d respectively. As illustrated in FIGS. 3A-3D, 4A-4C and 4D, the extensions 118a, 118b and 118c have a free end (not connected to the stent lattice) when the stent is deployed to its expanded or deployed state. In accordance with the present invention, the extension 118a, 118b and 118c can comprise a different material from the remainder of the components used for the stent lattice (for instance the hoops, loops, struts and bridges) especially if a different stiffness is desired.

Figure 4A:
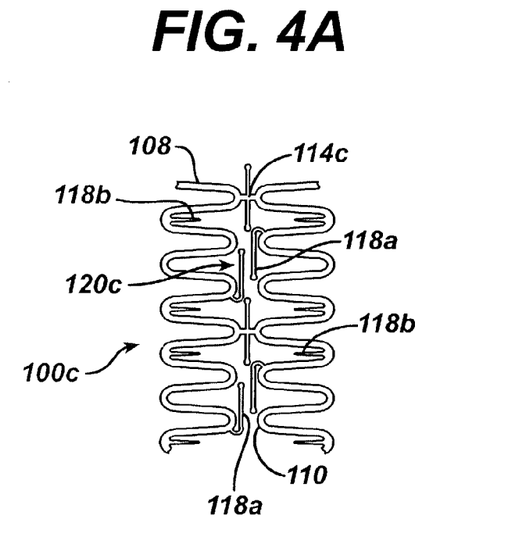
FIG. 4A is a partial side view of a stent having an open-cell design with one or more extensions in accordance with the present invention.
Figure 4B:
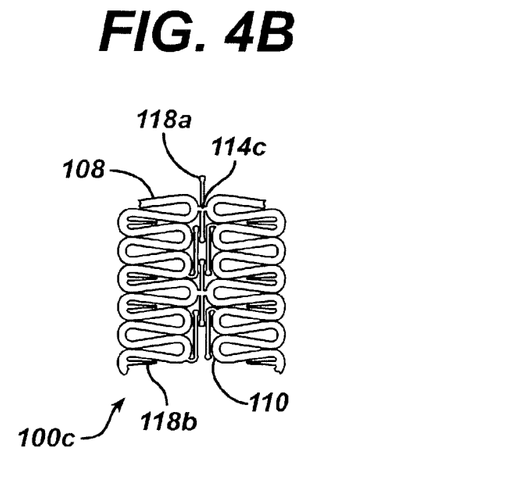
FIG. 4B is a partial side view of the stent of FIG. 4A in a crimped state in accordance with the present invention.
Figure 4C:
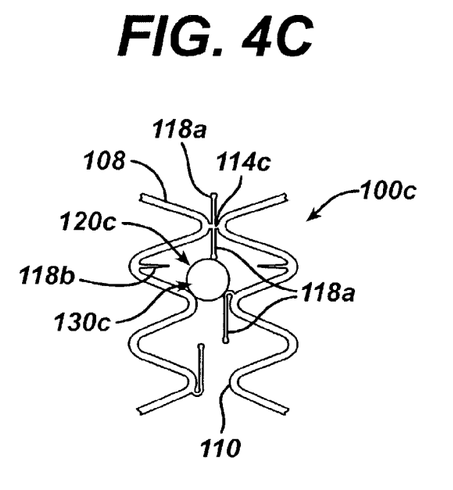
FIG. 4C is a partial side view of the stent of FIG. 4A in an expanded stent in accordance with the present invention.

As shown in FIGS. 4A-4C, the stent 100c in accordance with the present invention is an open-cell design stent having a plurality of cells 120c (FIGS. 4A and 4C) and having extensions 118a (connected at loops 110 according to a specific sequence of loops 110) and extensions 118b connected at the inner most portion of the loops 110 (for example in the middle of each hoop which extend into the cell 120c and help define a maximum circular diameter 130c). As shown in FIG. 4C, when the stent 100c is deployed to its expanded state, i.e. at about or approximately 3.0 mm for the overall stent diameter in one embodiment (approximately 3.0 mm overall diameter along the longitudinal axis 103), the cell 120c has a maximum circular cell diameter 130c having a size which ranges from about 0.76 mm to about 1.22 mm. Preferably, the cell 120c has a maximum circular diameter 130c which ranges from about 0.91 mm to about 1.12 mm after deployment (in its expanded state), e.g. expanded to an overall stent diameter of approximately 3.0 mm along longitudinal axis 103. Alternatively or additionally, the cell 120c has a maximum circular diameter 130c ranging from about 0.76 mm to about 1.02 mm after deployment to its expanded state (expanded to an overall stent diameter of about 3.0 mm as measured along its longitudinal axis)

After deployment to its expanded state, it may also be desirable to dilate the cell 120c through a cell dilation procedure, for example, a side branch access procedure. Thus, when the cell 120c of stent 100c is dilated (through a side access procedure), after the stent 100c is deployed, the cell 120c will have a maximum circular cell diameter 130c having a size that is greater than 3.0 mm after dilation of the cell 120c. Preferably, the cell 120c is dilated to a maximum circular cell diameter 130c that is about or approximately 3.0 mm after dilation of the cell 120c as part of a side branch access procedure. More preferably, the cell 120c is dilated to a maximum circular cell diameter 130c ranging from approximately 3.0 mm to about or approximately 3.5 mm when the cell 120c is dilated. Again, in general, the maximum circular diameter 130c is defined by the components of the stent lattice such as the struts 108, loops 110 and the extensions 118a and 118b as shown.

As illustrated in FIG. 4B, when the stent 100c is in its crimped state, i.e. crimped onto a stent delivery device such as a catheter, the extensions 118a connected to loops 110 will nest and/or lie in juxtaposition with or adjacent to each other.

Figure 4D:
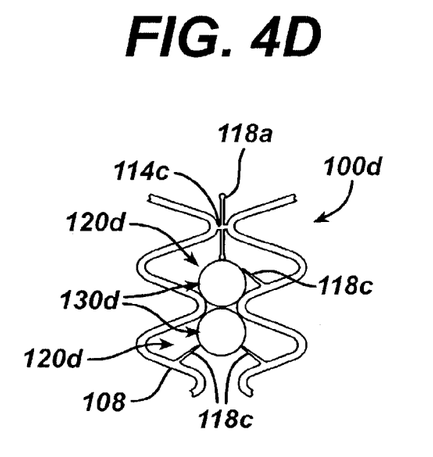
FIG. 4D is a partial side view of an alternative embodiment of an open-cell design stent in the expanded state in accordance with the present invention having one or more extensions extending from the struts and bridges in accordance with the present invention.

In accordance with the present invention, the stent 100d is an alternative embodiment of an open-cell design wherein extensions 118c are located on the struts 108 and extend into open-cell 120d and along with extensions 118a connected to bridges 114c, define a maximum circular cell diameter 130d. Again, similar to the previously described embodiments for the stent in accordance with the present invention, after the stent 100d has been deployed/expanded, for example to an overall stent diameter of about or approximately 3.0 mm, the cell 120b has a maximum circular diameter 130d having a size which ranges from about 0.76 mm to about 1.22 mm (when the stent 100d is deployed to its expanded state at an overall stent diameter of about or approximately 3.0 mm. i.e. approximately 3.0 mm diameter along longitudinal axis 103), and preferably, (if a side branch access procedure may be desired), the maximum circular cell diameter 130d has a size which ranges from about 0.91 mm to about 1.12 mm when the stent 100d is deployed to its expanded state at an overall stent diameter of about or approximately 3.0 mm as measured along longitudinal axis 103.

Preferably, when no side branches are present, the stent 100d has cells 120d comprising a maximum circular diameter ranging from about 0.76 mm to about 1.02 mm when the stent 100d is expanded to its deployed state at an overall stent diameter of about 3.0 mm (as measured around the longitudinal axis of the stent).

Additionally, after deployment of the stent 100d (in this example to an overall stent diameter of approximately 3.0 mm as measured along longitudinal-axis 103), it may also be desirable to conduct a cell dilation procedure, for example, a side branch access procedure on the cell 120b. And, since the stent 100d has an open cell 120d as shown in FIG. 4D, when the cell 120d is dilated, the cell 120d will be dilated such that it has a maximum circular cell diameter 130d having a size that is greater than 3.0 mm. And alternatively or additionally, the cell 120d is dilated such that the cell 120d has a maximum circular cell diameter 130d having a size that is at about or approximately 3.0 mm when the cell 120d is dilated. Preferably, when the cell 120d is dilated, the cell 120d has a maximum circular cell diameter 130d ranging from about 3.0 mm to about 3.5 mm.

In the example of the present invention shown in FIGS. 3A-3D, each bridge 114b has two apexes 116 on one side and two apexes 116 on an opposite side thereof. Moreover, an extension 118 is integrally formed with and protrudes from the bridge 114b at each of these apexes 118 on both sides of the bridge 114b as shown. It is important to note that the present invention should not be limited by the specific design illustrated in FIGS. 3A-3D or specific designs shown in FIGS. 4A-4D. It is within the intention and scope of the present invention to also include bridge designs for both open-cell (FIGS. 4A-4D) and closed-cell stents (FIGS. 3A-3D) having alternative configurations with one or more extensions 118, 118a, 118b, and/or 118c respectively thereon which may or may not have the ability to nest or be positionable with or alignable with such that they are juxtaposition and adjacent extensions 118, 118a, 118b, and/or 118c respectively of adjacent bridges 114b, 114a and 114d respectively.

Nested extensions or fingers 118a, 118b, 118c and 118d of the stent 100b, 100c and 100d respectively in accordance with the present invention have several advantages over the prior art stents 100 and 100a. For instance, the nested extensions not only reduce the interior space within the cells (either open-cell or closed-cell) due to the projection of the extensions 118 therein, but also, enhance the overall surface area of the stent. The increased surface area within the space or area defined by the stent lattice including the extensions, provides a significant advantage of preventing the prolapse of plaque or tissue into the cell and ultimately into the lumen of the stent when deployed within a vessel, i.e. at the site of a lesion within the vessel. Accordingly, the extensions or fingers 118a, 118b, 118c and 118d respectively in accordance with the present invention inhibit this prolapse phenomena thereby providing a barrier against restenosis of the vessel at the lesion site. As mentioned above, the interior space of the cells (either closed cell 120b or open cell 120c and 120dc respectively) is decreased in a substantial manner. For instance, the extensions or fingers 118a, 118b, 118c and 118d result in a maximum circular cell diameter size 130c and 130d respectively having a decrease ranging as high as 54% of a maximum circular cell diameter size for a stent without extensions or fingers such as the prior art stents shown in FIGS. 1A-1D and 2A-2C.

Additionally, due to the nested alignment of the extensions or fingers 118a, 118b, 118c and 118d respectively in accordance with the present invention, the extensions or fingers do not make up a continuous element that requires it to plastically deform during expansion of the stent 100b, 100c and 100d respectively in that there is no stress or strain that is transmitted by the extensions or fingers when the stent is deployed or expanded to its expanded state due to the free or unconnected end of the extensions. As is known in the art, continuous elements that interact with stent components in general, tend to stretch during deployment resulting in strain and stress from the expansion of the radial rings (strain-stress from the expansion of the radial rings are transmitted into the flex connector). The free or unconnected end of the extensions 118a, 118b, 118c and 118d respectively prevent this strain and stress from occurring.

Furthermore, another advantage of the extension 118a, 118b, 118c and 118d respectively (due to its finger-like projection design) in accordance with the stent of the present invention, is that the nesting or juxtaposition or adjacent alignment of these projections or extensions may prevent flex connector longitudinal collapse which is commonly seen at the ends 102 and 104 of known stents 100 and 100a as they expand.

In accordance with the present invention, the extensions or fingers 118a, 118b, 118c and 118d respectively may also take the form of shapes such as those patterns mentioned above for providing a nesting or juxtaposition arrangement between adjacent bridges 114a.

Additionally, the stent 100b, 100c and 100d in accordance with the present invention may be made from various materials such as those referred to above. For example, the stent 100b, 100c and 100d is made of an alloy such as stainless steel. Moreover, the stent 100b, 100c and 100d is alternatively made of a crush-recoverable material such as a superelastic material or superelastic alloy. In particular, the stent 100b, 100c and 100d is made of nickel titanium (NiTi) thereby providing it with superelastic and crush recoverable properties as a self-expanding stent.

Another major advantage of the extensions 118a, 118b, 118c and 118d respectively, is that the extensions provide enhanced and/or additional coverage and support at the ostium of a vessel side branch when either the closed cell 120b or the open cell 120c and 120d respectively undergo a dilation of the cell 120b, 120c and 120d respectively as part of a side-branch access procedure such as the one described above. Thus, upon dilation of the respective cell, the extensions 118a, 118b, 118c and 118d respectively are cleared from flow passage at the vessel side branch due to balloon expansion, and the extensions 118a, 118b, 118c and 118d respectively are moved into a support position (by the balloon expansion) for directly supporting the side branch vessel thereby forming a stable graft at the main vessel and side branch vessel junction.

Another major advantage of the present invention is to minimize the number of flexible links (connections between adjacent hoops) for a stent while minimizing the maximum circular cell diameter of the cells.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A stent comprising:
a lattice defining a substantially cylindrical configuration having a first open end and a second open end, the lattice having a crimped state and an expanded configuration, the lattice having a plurality of adjacent loops; a plurality of bridges connecting adjacent hoops; a plurality of extensions on the lattice; and each of the hoops, bridges and extensions defining a cell and wherein in the expanded configuration, the plurality of extensions extend into the cell defining a maximum cell diameter, the extensions having one end integrally formed with the lattice and another end extending into the cell and wherein the stent in the expanded configuration has a maximum expanded cell diameter ranging from about 0.76 mm to about 1.22 mm due to the plurality of extensions.

2. The stent according to claim 1, wherein the maximum expanded diameter ranges from about 0.91 mm to about 1.22 mm.

3. The stent according to claim 1, wherein the maximum expanded cell diameter ranges from about 0.76 mm to about 1.02 mm.

4. The stent according to claim 1, wherein the stent has a maximum cell diameter ranging from about 1.5 mm to about 3.5 mm when the cell is dilated.

5. The stent according to claim 4, wherein the stent has a maximum cell diameter ranging from about 1.5 mm to about 3.0 mm when the cell dilated.

6. The stent according to claim 4, wherein the stent has as a closed cell design.

7. The stent according to claim 1, wherein the stent has a maximum cell diameter ranging from about 3.0 mm to about 3.5 mm when the cell is dilated.

8. The stent according to claim 1, wherein the stent has a maximum cell diameter of up to about 3.5 mm when the cell is dilated.

9. The stent according to claim 8, wherein the stent has as an open cell design.

10. The stent according to claim 1, wherein the stent has a maximum cell diameter of approximately 3.0 mm when the cell is dilated.

11. The stent according to claim 1, wherein the stent has a maximum cell diameter ranging from about 3.0 mm to about 3.5 mm when the cell is dilated.

12. The stent according to claim 1, wherein each hoop comprises a plurality of struts.

13. The stent according to claim 1, wherein the extensions are located on the bridges.

14. The stent according to claim 1, wherein the extensions are located on the hoops.

15. The stent according to claim 14, wherein the extensions are located on the loops.

16. The stent according to claim 14, wherein the extensions are located on the struts.

17. The stent according to claim 16, wherein the extensions are located on at least one of the loops and the struts.

18. The stent according to claim 17, wherein the extensions are located on the bridges.

19. The stent according to claim 1, further comprising a drug on one or more portions of the lattice.

20. The stent according to claim 19, further comprising a drug and polymer combination on one or more portions of the lattice.

21. The stent according to claim 20, wherein the drug comprises rapamycin.

22. The stent according to claim 20, wherein the drug comprises paclitaxel.

23. The stent according to claim 1, wherein the extensions do not plastically deform during expansion of the stent.

24. The stent according to claim 1, wherein the end of the extension extending into the cell does not contact any other part of the stent structure.

25. The stent according to claim 1, wherein the extensions decrease maximum circular cell diameter size by about 54%.

* * * * *